United States Patent [19]

Akasaki et al.

[11] Patent Number: 5,011,757
[45] Date of Patent: Apr. 30, 1991

[54] ELECTROPHOTOGRAPHIC PHOTORECEPTOR CONTAINING A FLUORENE DERIVATIVE

[75] Inventors: Yutaka Akasaki; Katsumi Nukada; Katsuhiro Sato, all of Kanagawa, Japan

[73] Assignee: Fuji Xerox Co., Ltd., Tokyo, Japan

[21] Appl. No.: 436,875

[22] Filed: Nov. 15, 1989

[30] Foreign Application Priority Data

Nov. 16, 1988 [JP] Japan .................. 63-287613
Nov. 16, 1988 [JP] Japan .................. 63-287618
Nov. 16, 1988 [JP] Japan .................. 63-287620
Nov. 16, 1988 [JP] Japan .................. 63-287621

[51] Int. Cl.$^5$ .......................... G03G 5/06; G03G 5/14
[52] U.S. Cl. .............................. 430/58; 430/72
[58] Field of Search .................. 430/72, 58, 59

[56] References Cited
U.S. PATENT DOCUMENTS 4,853,308  8/1989  Ong et al. ...................... 430/72

Primary Examiner—David Welsh
Attorney, Agent, or Firm—Finnegan, Henderson, Farabow, Garrett, and Dunner

[57] ABSTRACT

An electrophotographic photoreceptor comprising a conductive substrate and a photosensitive layer on the conductive substrate, wherein the photosensitive layer contains a compound of formula (I) as a charge transporting agent:

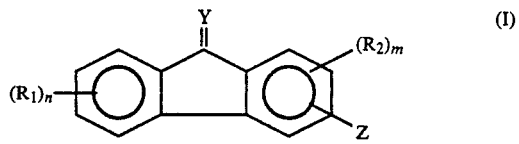

(I)

wherein $R_1$ and $R_2$ each represents a hydrogen atom, an alkyl group, an aryl group, an alkoxycarbonyl group, an aryloxycarbonyl group, a nitro group, a halogen atom, an alkylcarbonyl group or an arylcarbonyl group; Y represents

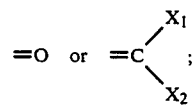

$X_1$ and $X_2$ may be the same or different groups and are selected from a cyano group or an alkoxycarbonyl group; Z represents

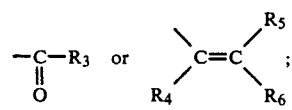

$R_3$ represents a substituted or unsubstituted aryl or nitrogen-containing heterocyclic group; $R_4$, $R_5$ and $R_6$ each represents a hydrogen atom, an alkyl group, an aralkyl group, an aryl group or a heterocyclic group; when Z is the

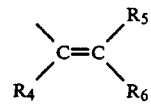

group, $R_1$ and $R_2$ are not the alkylcarbonyl group; m is 0 or 1; n is 0 to 2; and when n is 2, the $R_1$ groups may be the same or different.

15 Claims, No Drawings

ELECTROPHOTOGRAPHIC PHOTORECEPTOR CONTAINING A FLUORENE DERIVATIVE

FIELD OF THE INVENTION

This invention relates to an electrophotographic photoreceptor for forming an electrostatic latent image.

BACKGROUND OF THE INVENTION

Electrophotographic photoreceptors containing organic photoconductive materials have been extensively studied because such photoreceptors do not cause environmental pollution, have high productivity and are inexpensive. There are known electrophotographic photoreceptors wherein the photosensitive layer contains diphenyldicyanoethylene derivatives as the sensitizing agent. Such a photoreceptor is disclosed in JP-A-54-30834 (the term "JP-A" refers to an unexamined published Japanese patent application).

However, a problem with such use of organic photoconductive materials is that materials which absorb visible light and generate electric charges exhibit poor charge retention characteristics; whereas materials having good charge retention characteristics and excellent film forming properties barely exhibit photoconductivity by visible light. In order to solve these problems, the prior art used a photosensitive layer of a laminate type composed of a layer containing a charge generating agent which absorbs visible light and generates electric charges and another layer containing a charge transporting agent which transports the charges produced. Various charge transporting agents have been proposed. For example, when the charge transporting agent is of the positive hole transporting agent type, amine compounds, hydrazone compounds, pyrazoline compounds, oxazole compounds, oxadiazole compounds, stilbene compounds and carbazole compounds can be used. Also, the other charge transporting agent, i.e., of the electron transporting agent type is 2,4,7-trinitrofluorenone (TNF) for example. Other examples of charge transporting agents include compounds containing boron described in JP-B-48-9988 (the term "JP-B" refers to an examined Japanese patent publication) and Canadian Patent 912,019.

As yet, no completely satisfactory sensitizing agent has been found for use in single layer structure type electrophotographic photoreceptors using an organic photoconductive material. For electrophotographic photoreceptors having a laminated structure, a positively charging type is preferred from the viewpoints of preventing ozone generation due to corotron and of controlling the charging of the toner in development. When the laminated type layer electrophotographic photoreceptor is of the positively charging type and when the charge transporting agent is of the positive hole transporting type, it is necessary that the charge generating layer be the upper layer. However, because the custom is to make the charge generating layer thin, the problem arises that such a thin charge generating layer is insufficiently thick to meet the mechanical requirements of the photoreceptor. Thus, it is imperative to use a positively charging photoreceptor with a sufficiently thick charge transporting layer as the upper layer. To provide such a desired photoreceptor, it is necessary to use an electron transporting agent in the charge transporting layer. However, the prior art charge transporting agents are not sufficiently effective as electron transporting agents.

The present invention is intended to overcome the above noted problems associated with the prior art.

SUMMARY OF THE INVENTION

Accordingly, an object of the present invention is to provide an electrophotographic photoreceptor having excellent electrophotographic characteristics.

Another object of the present invention is to provide a positively charging laminated type electrophotographic photoreceptor having excellent electrophotographic characteristics.

The present inventors have found that a positively charging type electrophotographic photoreceptor having excellent characteristics can be obtained when the charge transporting agent is selected from a group of fluorene derivatives.

Accordingly, the present invention provides an electrophotographic photoreceptor comprising a conductive substrate and a photosensitive layer on the conductive substrate, wherein the photosensitive layer comprises, as a charge transporting agent, a compound of formula (I):

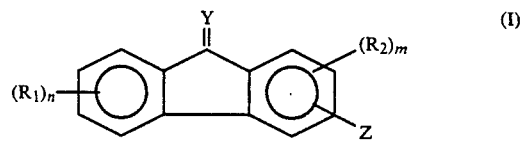

In formula (I), $R_1$ and $R_2$ each represents a hydrogen atom, an alkyl group, an aryl group, an alkoxycarbonyl group, an aryloxycarbonyl group, a nitro group, a halogen atom, an alkylcabonyl group or an arylcarbonyl group; Y represents

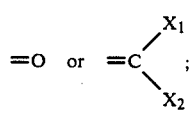

$X_1$ and $X_2$ may be the same or different and are selected from a cyano group or an alkoxycarbonyl group; Z represents

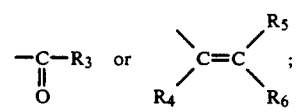

$R_3$ represents a substituted or unsubstituted aryl or nitrogen-containing heterocyclic group; $R_4$, $R_5$ and $R_6$ each represents a hydrogen atom, an alkyl group, an aralkyl group, an aryl group or a heterocyclic group; when Z is the

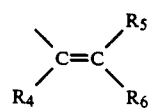

group, $R_1$ and $R_2$ are other than the alkylcarbonyl group; m is 0 or 1; n is 0 to 2; and when n is 2, the $R_1$ groups may be the same or different.

DETAILED DESCRIPTION OF THE INVENTION

In formula (I), $R_1$ and $R_2$ each represents a hydrogen atom, an alkyl group preferably having 1 to 8 carbon atoms, an aryl group preferably having 6 to 12 carbon atoms, an alkoxycarbonyl group preferably having 2 to 15 carbon atoms, aryloxycarbonyl group preferably having 7 to 20 carbon atoms, a nitro group, a halogen atom, an alkylcarbonyl group preferably having 2 to 9 carbon atoms, or an arycarbonyl group preferably having 7 to 20 carbon atoms. The alkoxycarbonyl group for $X_1$ and $X_2$ preferably has 2 to 10 carbon atoms. $R_3$ represents an ary group preferably having 6 to 20 carbon atoms or a nitrogen-containing heterocyclic group such as a pyridyl group and a quinolyl group, which may be substituted. $R_4$, $R_5$ and $R_6$ each represents a hydrogen atom, an alkyl group preferably having 1 to 8 carbon atoms, an aralkyl group preferably having 7 to 21 carbon atoms, an aryl group preferably having 6 to 21 carbon atoms or a heterocyclic group such as a pyridyl group and a quinolyl group.

The compounds of formula (I) can be further classified into compounds represented by more specific structural formulas (Ia), (Ib), (Ic) and (Id). Examples of these compounds include the following compounds. In the formulas, $X_1$, $X_2$, $R_1$, $R_2$, $R_3$, $R_4$, $R_5$, $R_6$, m and n are as defined above in formula (I).

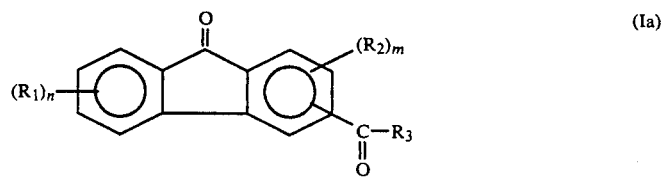

(Ia)

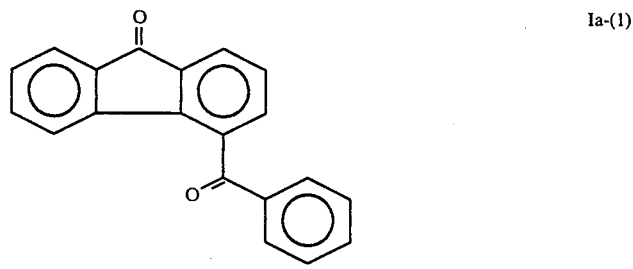

Ia-(1)

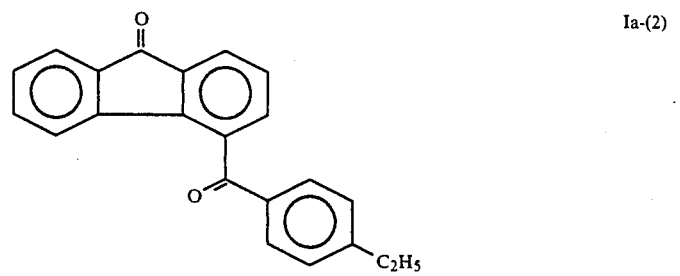

Ia-(2)

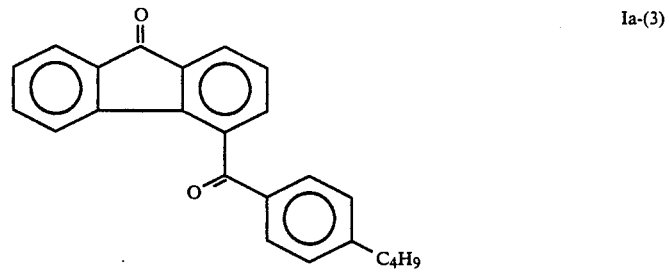

Ia-(3)

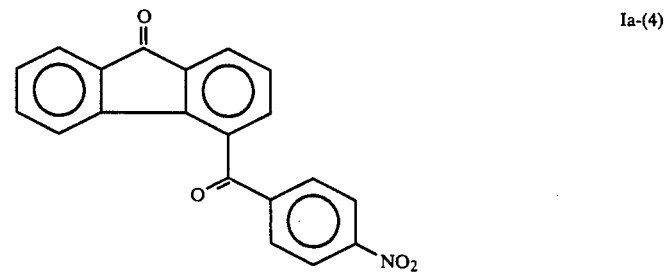

Ia-(4)

-continued
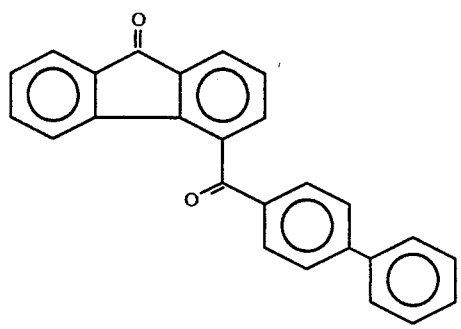
Ia-(5)
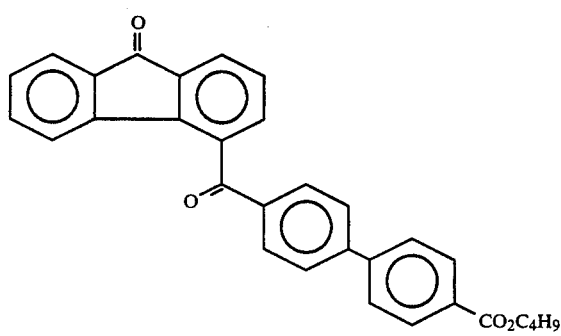
Ia-(6)
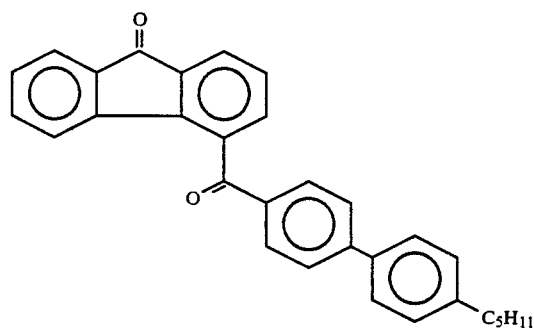
Ia-(7)
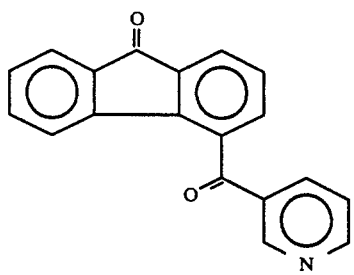
Ia-(8)
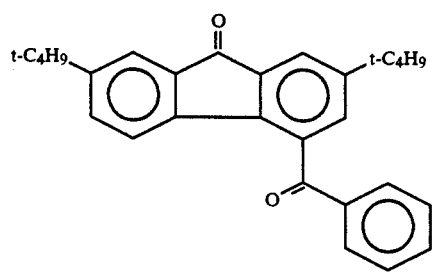
Ia-(9)

-continued
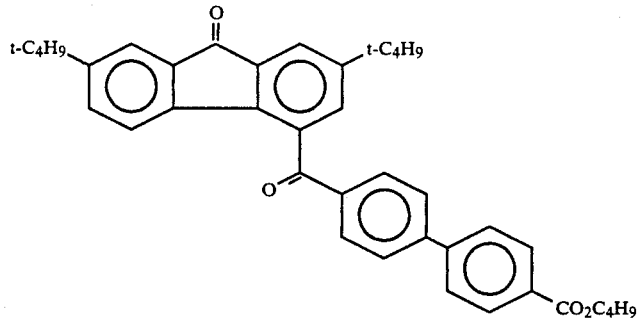
Ia-(10)
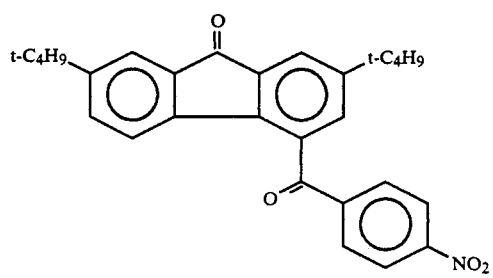
Ia-(11)
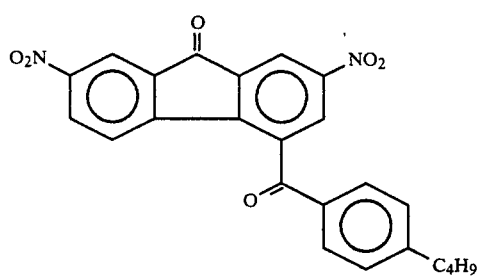
Ia-(12)
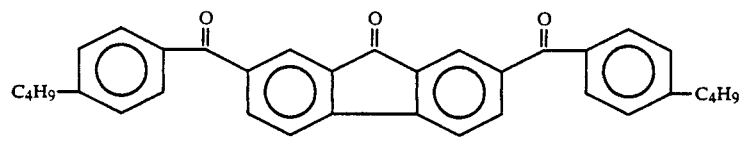
Ia-(13)
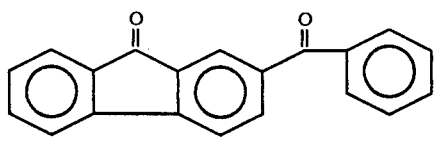
Ia-(14)
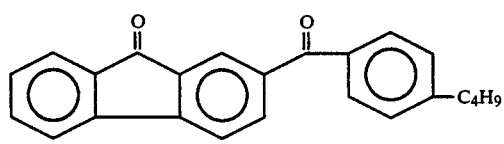
Ia-(15)
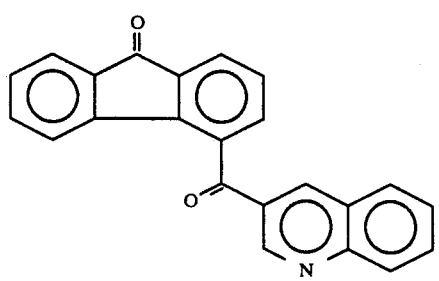
Ia-(16)

-continued
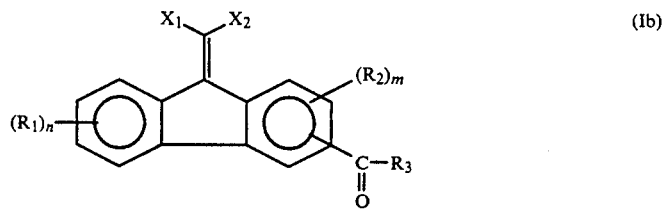 (Ib)
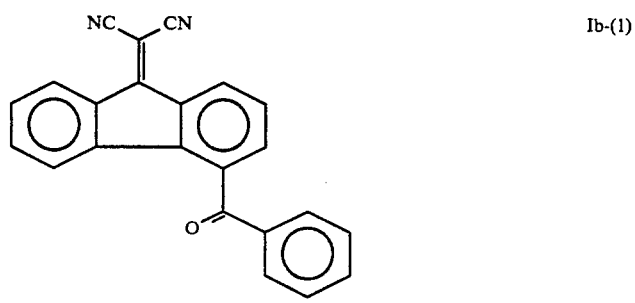 Ib-(1)
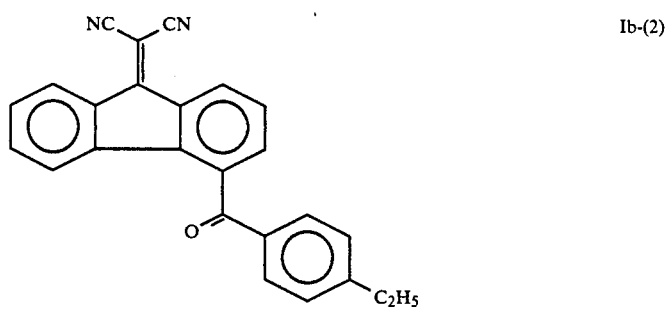 Ib-(2)
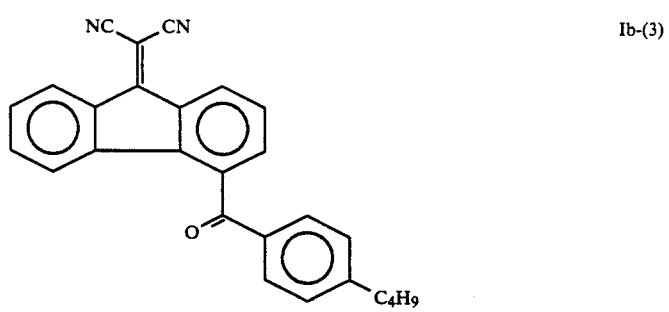 Ib-(3)
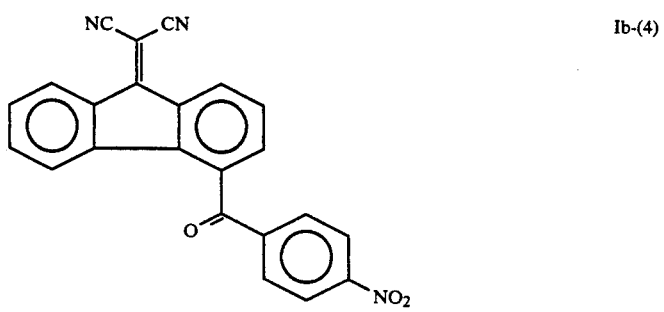 Ib-(4)

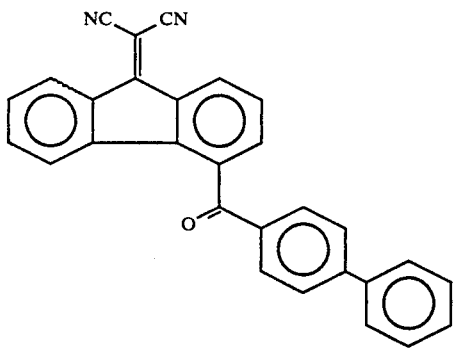
Ib-(5)
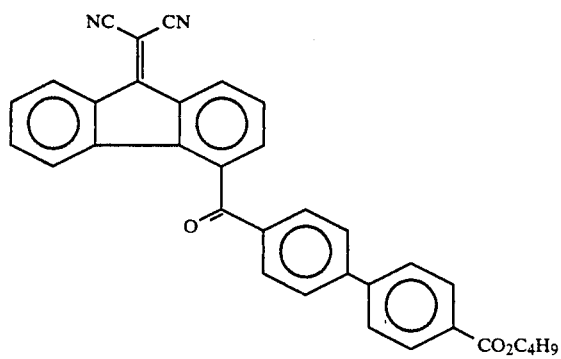
Ib-(6)
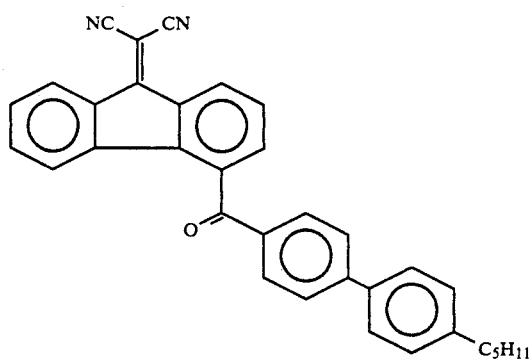
Ib-(7)
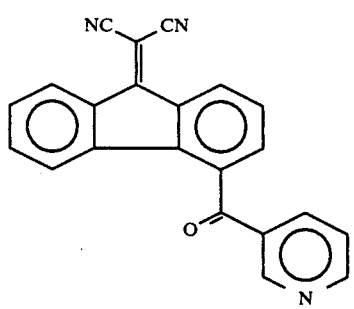
Ib-(8)
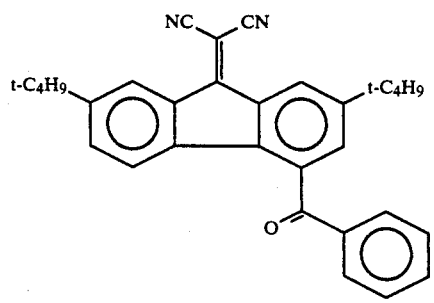
Ib-(9)

-continued
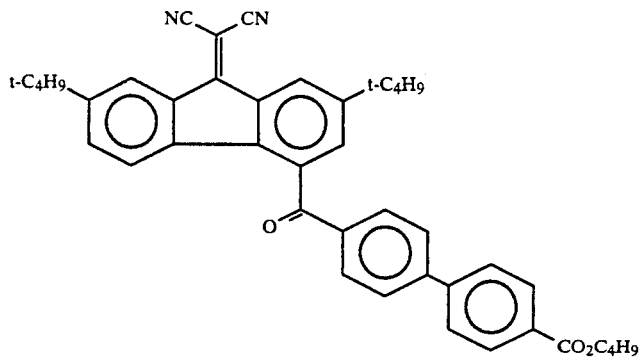
Ib-(10)
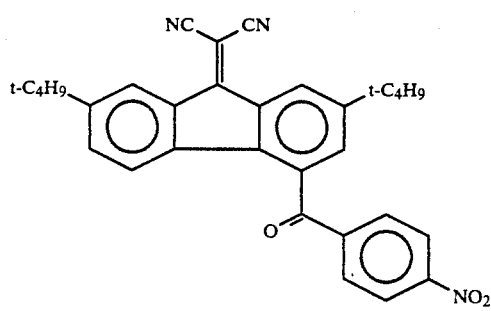
Ib-(11)
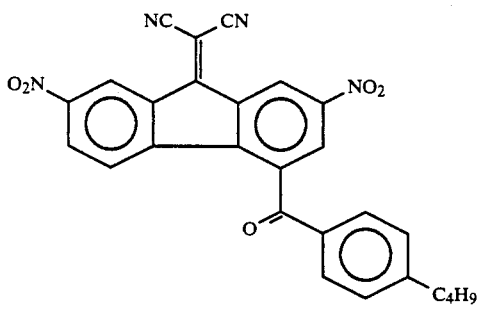
Ib-(12)
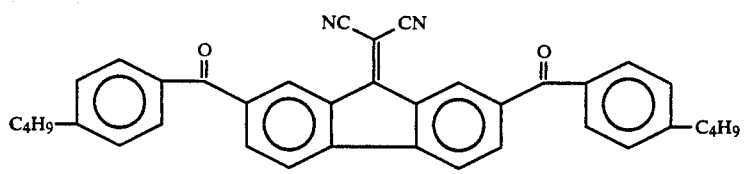
Ib-(13)
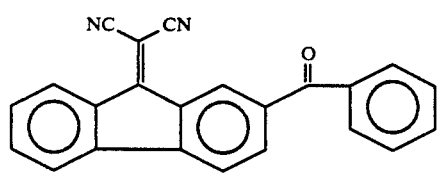
Ib-(14)
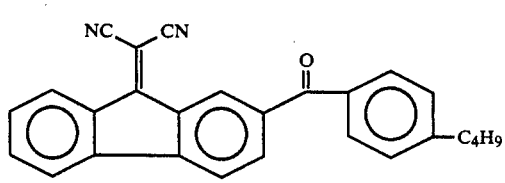
Ib-(15)

-continued
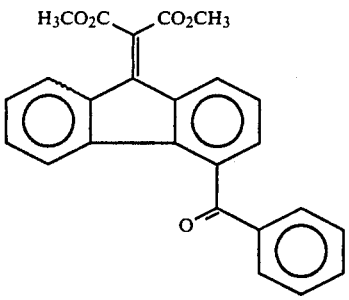 Ib-(16)
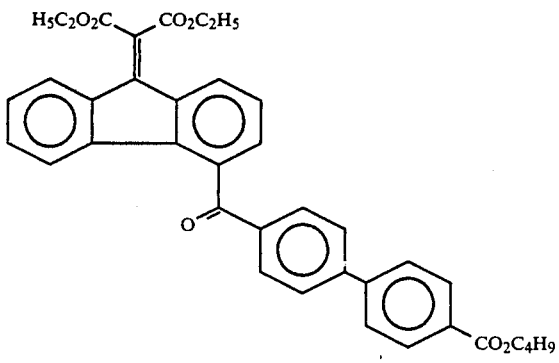 Ib-(17)
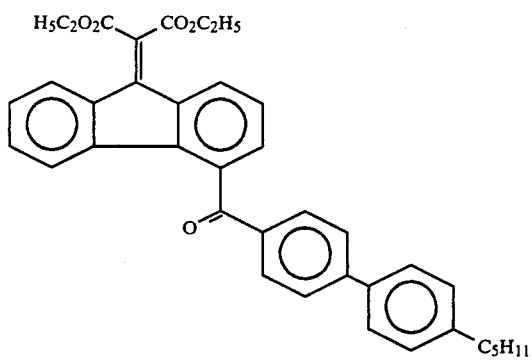 Ib-(18)
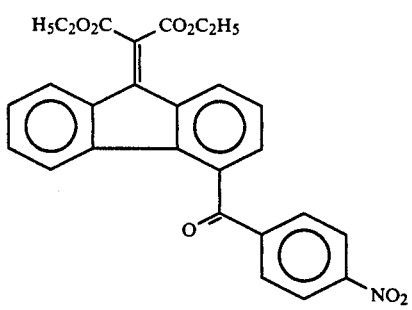 Ib-(19)
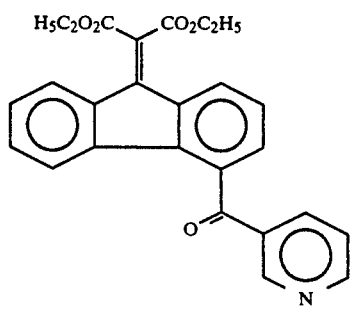 Ib-(20)

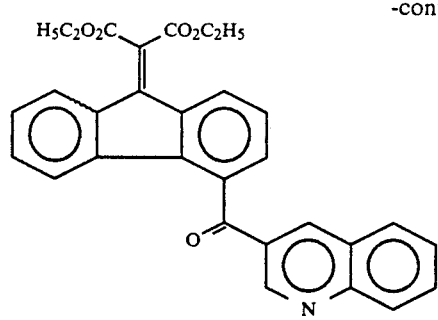
Ib-(21)
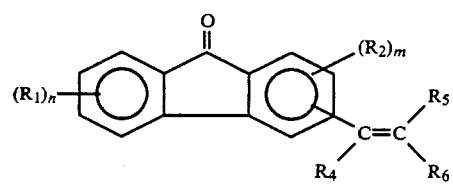
(Ic)
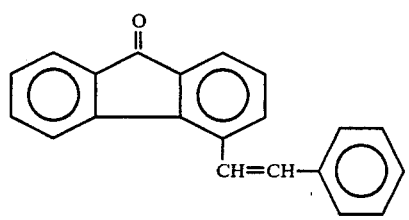
Ic-(1)
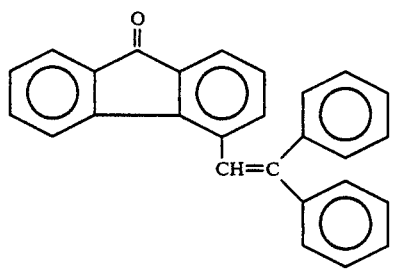
Ic-(2)
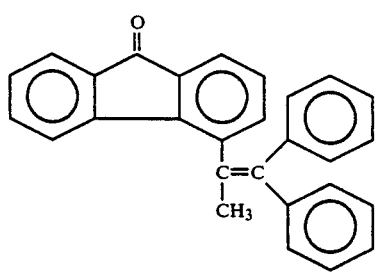
Ic-(3)
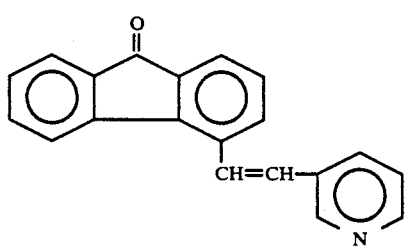
Ic-(4)
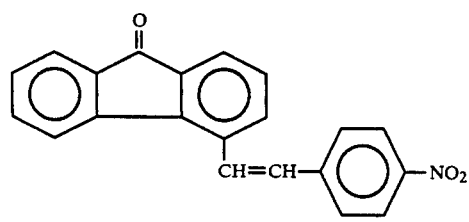
Ic-(5)

-continued
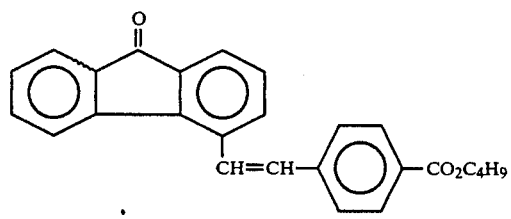
Ic-(6)
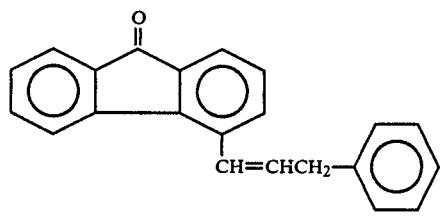
Ic-(7)
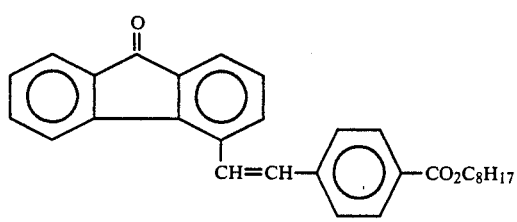
Ic-(8)
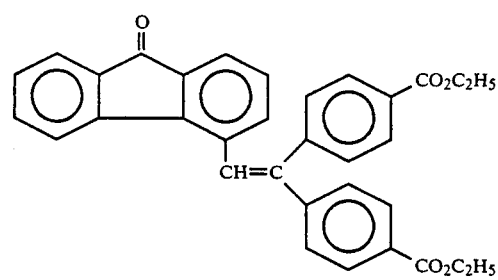
Ic-(9)
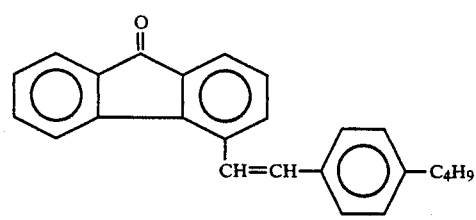
Ic-(10)
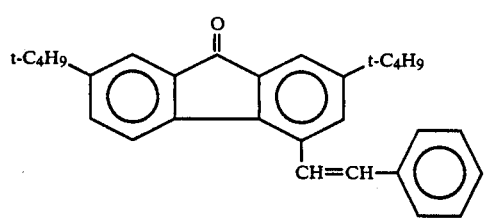
Ic-(11)
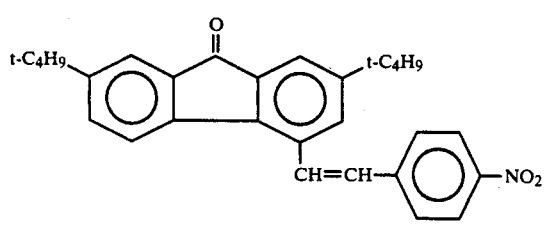
Ic-(12)

-continued
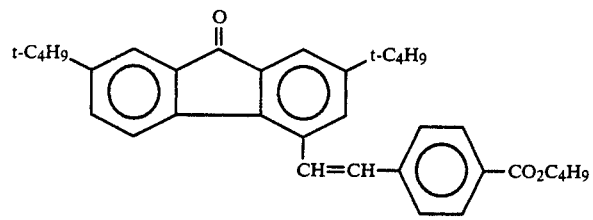
Ic-(13)
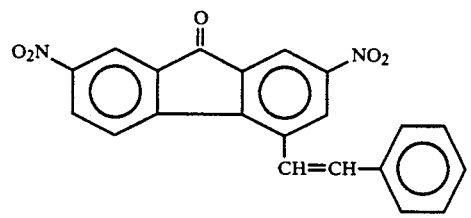
Ic-(14)
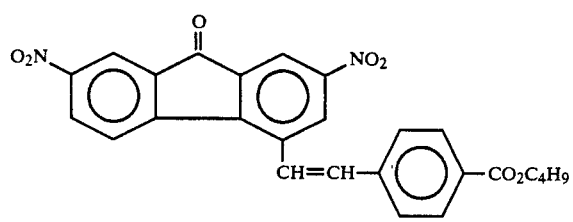
Ic-(15)
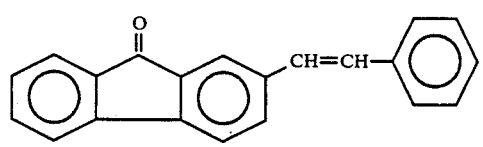
Ic-(16)
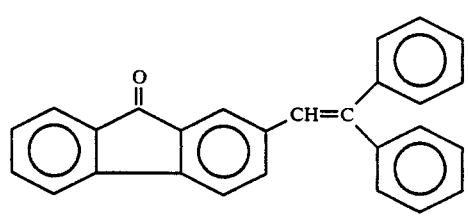
Ic-(17)
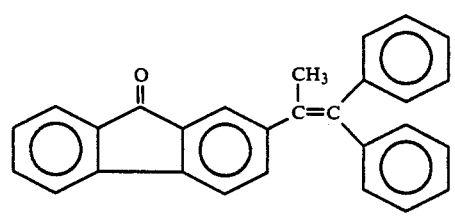
Ic-(18)
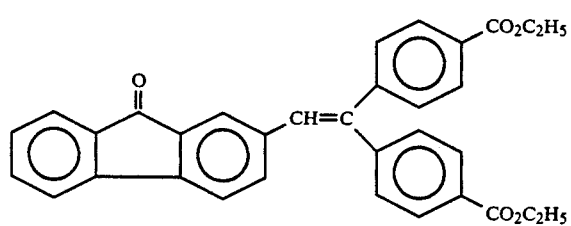
Ic-(19)

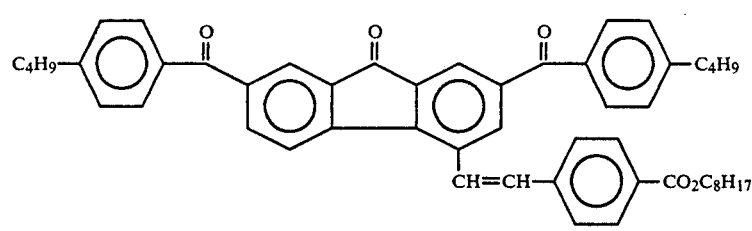
Ic-(20)
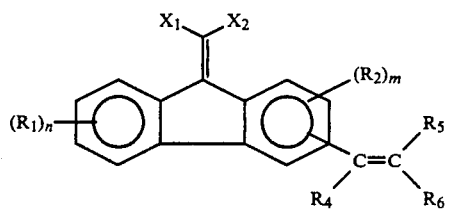
(Id)
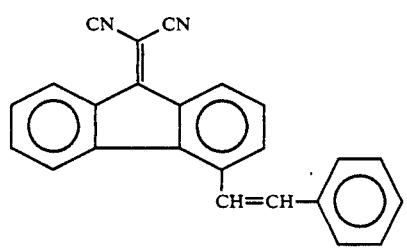
Id-(1)
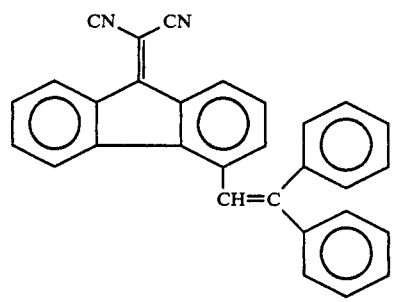
Id-(2)
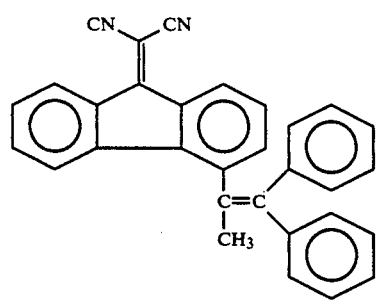
Id-(3)
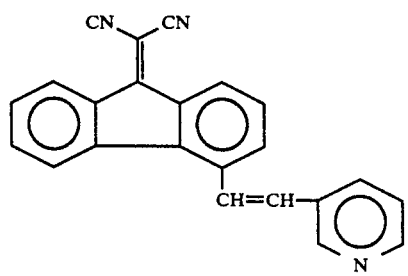
Id-(4)

-continued
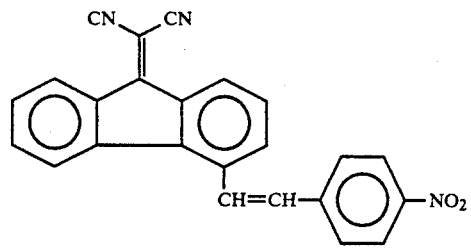
Id-(5)
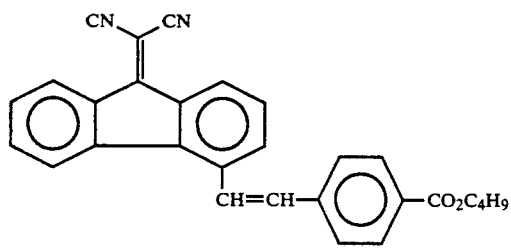
Id-(6)
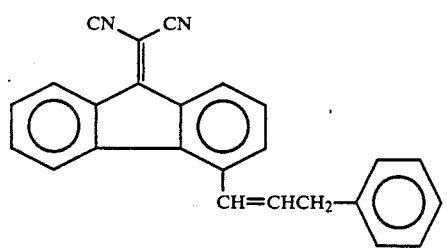
Id-(7)
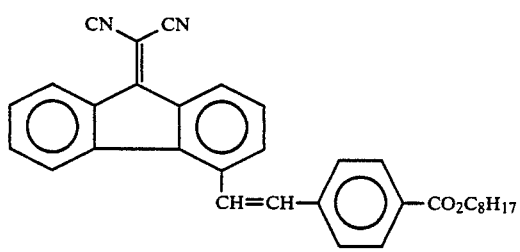
Id-(8)
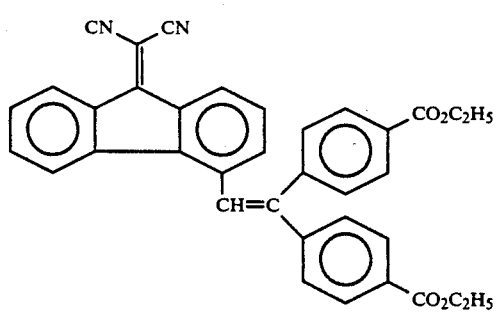
Id-(9)
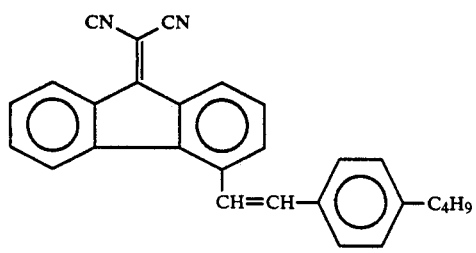
Id-(10)

-continued
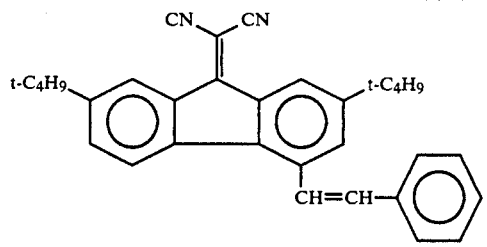
Id-(11)
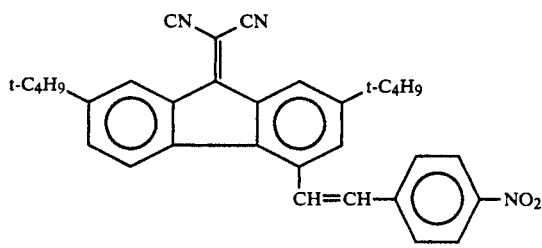
Id-(12)
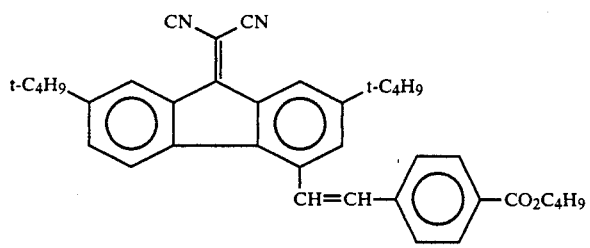
Id-(13)
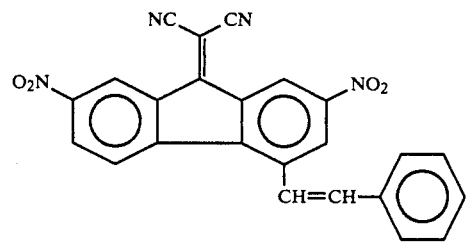
Id-(14)
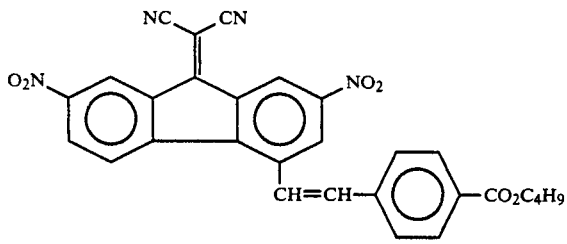
Id-(15)
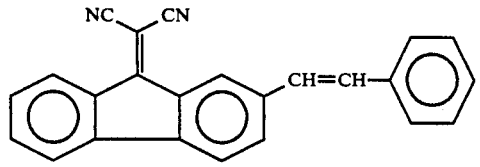
Id-(16)
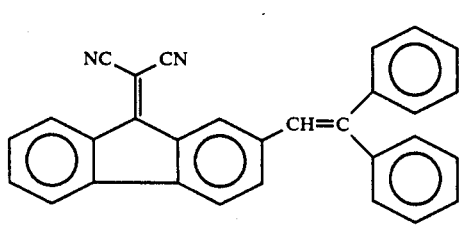
Id-(17)

-continued
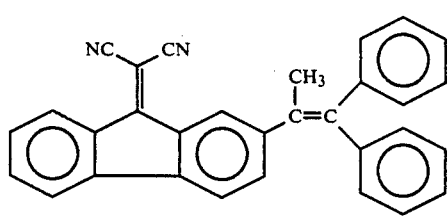
Id-(18)
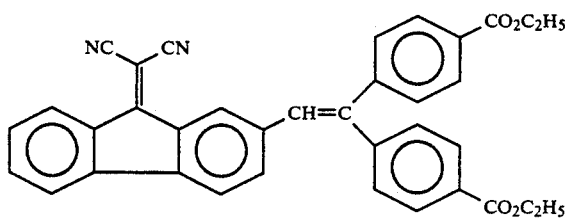
Id-(19)
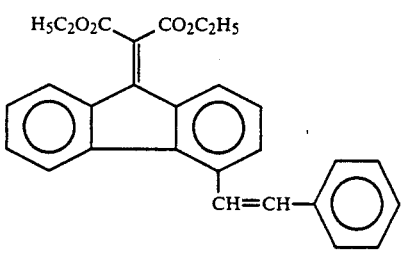
Id-(20)
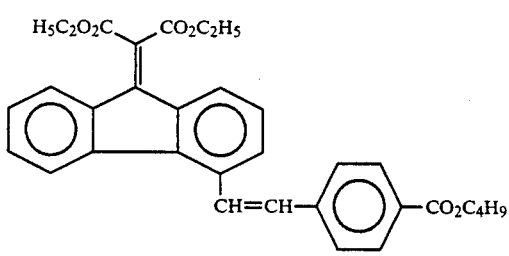
Id-(21)
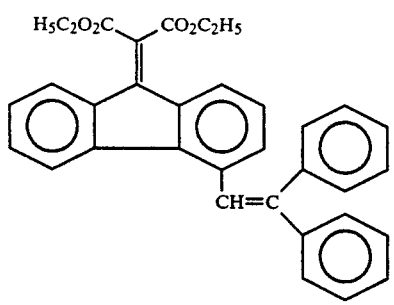
Id-(22)
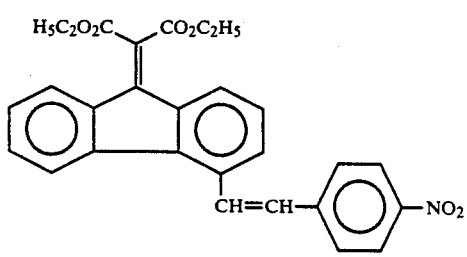
Id-(23)

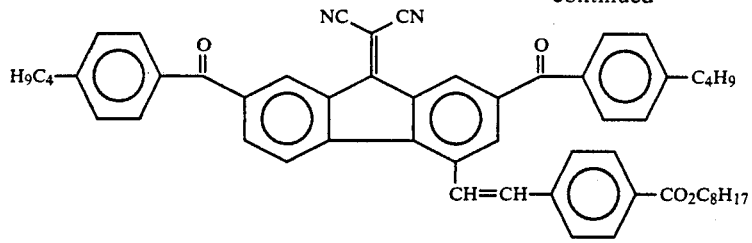

Id-(24)

The compounds of formulas (Ia) and (Ib) can be synthesized in the following manner as shown in the following reaction formula. A fluorenone carboxylic acid chloride of formula (II) is reacted with a compound of the formula R₃H to prepare a compound having the structure of formula (Ia). The compound of formula (Ia) and malonitrile are heated in a solvent such as pyridine under reflux to prepare a compound of formula (III). If desired, the compound of formula (III) is hydrolyzed, esterified or condensed with a malonic ester to prepare a compound having the structure of formula (Ib).

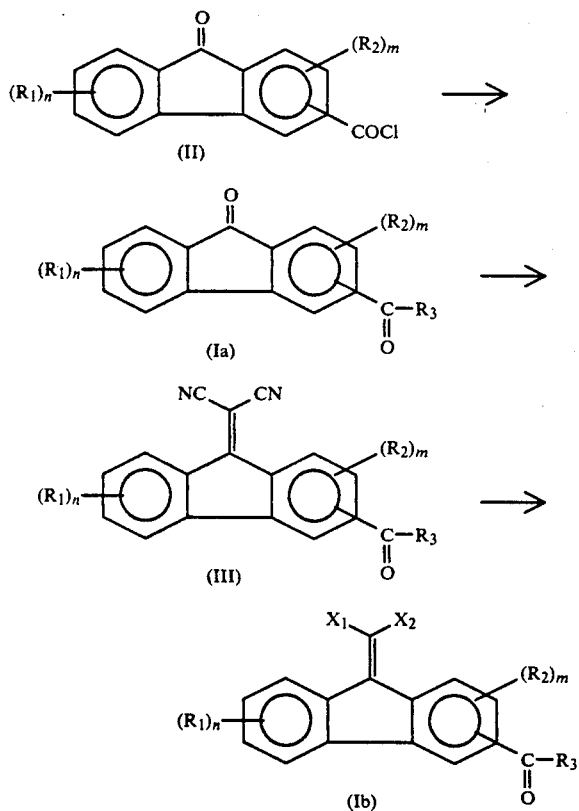

In the above cited formulas, $X_1$, $X_2$, $R_1$, $R_2$, $R_3$, m and n are as defined in formula (I).

The following synthesis examples illustrate the preparation of a number of compounds of formulas (Ia) and (Ib).

SYNTHESIS EXAMPLE 1

Synthesis of compounds Ia-(3) and Ib-(3)

25.0 g (111 mmol) of 9-fluorenone-4-carboxylic acid and 300 ml of thionyl chloride were placed in a 500 ml three-necked flask and refluxed in a nitrogen stream for 5 hours. Thionyl chloride was distilled off under reduced pressure. 100 ml of 1,2-dichloroethane was added to the residue and distillation was carried out under reduced pressure to remove residual thionyl chloride. 200 ml of methylene chloride was added to the formed acid chloride. The mixture was cooled in a cooling bath to −20° C. and 20.0 g (150 mmol) of aluminum chloride was added thereto. The mixture was stirred in a nitrogen stream for 15 hours. A solution consisting of 15.9 ml (118 mmol) of n-butylbenzene and 50 ml of methylene chloride was added dropwise thereto over a period of 30 minutes. After completion of the addition, stirring was continued for an additional 3 hours. The cooling bath was removed and stirring was continued at room temperature for 20 hours. Further, 7.5 g (56.3 mmol) of aluminum chloride was added. The mixture was stirred for 2.5 hours and 150 g of ice was added thereto. A 20% potassium hydroxide solution was added until the aluminum hydroxide dissolved. The organic layer was separated and the aqueous layer was extracted with methylene chloride to obtain an organic layer. The organic layers were combined and the solvent was distilled under reduced pressure. 200 ml of a 5% potassium hydroxide solution was added to the residue. The mixture was heated at 80° C. to decompose the residual acid chloride. The product was then extracted with methylene chloride and purified by means of silica gel short column (elution with methylene chloride). After the solvent was distilled off, the product was recrystallized from hexane and then ethyl acetate to obtain 13.8 g (yield: 36.4% by weight) of compound Ia-(3) as a yellow powder. The melting point is: 93°–95° C.

6.5 g of the thus-obtained fluorenone derivative Ia-(3), 1.3 g of malonitrile, 5 droplets of piperidine and 80 ml of methanol were placed in a 100 ml three-necked flask and refluxed in a nitrogen stream for 2 hours. The reaction mixture was cooled to room temperature. The thus precipitated crystal was recovered by filtration, washed with methanol, water and then methanol and recrystallized from methanol/CH₂Cl₂ to obtain 5 g (68%) of compound Ib-(3) as an orange cotton-like crystal. The melting point is: 156°–157° C.

SYNTHESIS EXAMPLE 2

Synthesis of compounds Ia-(5) and Ib-(5)

The procedure of Synthesis Example 1 was repeated except that biphenyl was used in place of n-butylbenzene. There were obtained compound Ia-(5) as a yellow needle-like crystal (melting point: 154.4°–156° C.) and compound Ib-(5) as an orange cotton-like crystal (melting point: 229°–230.5° C.).

SYNTHESIS EXAMPLE 3

Synthesis of compounds Ia-(7) and Ib-(7)

The procedure of Synthesis Example 1 was repeated except that pentylbiphenyl was used in place of n-butylbenzene. There were obtained compound Ia-(7) as a light yellow plate crystal (melting point: 151.5°–153°

C.) and compound Ib-(7) as an orange cotton-like crystal (melting point: 171°-172° C.).

Although only a few of the compounds encompassed by formulas (Ia) and (Ib) were illustratively prepared, methods similar to the methods described above can be used to synthesize the other compounds of formulas (Ia) and (Ib).

The compounds of formulas (Ic) and (Id) can be synthesized in the following manner as shown in the following reaction formula. A fluorene derivative of formula (IV) is oxidized in a solvent such as pyridine to prepare a compound having the structure of formula (Ic). The compound of formula (Ic) and malonitrile are heated in a solvent such as pyridine under reflux to prepare a compound of formula (V). If desired, the compound of formula (V) is hydrolyzed, esterified or condensed with a malonic ester to prepare a compound having the structure of formula (Id).

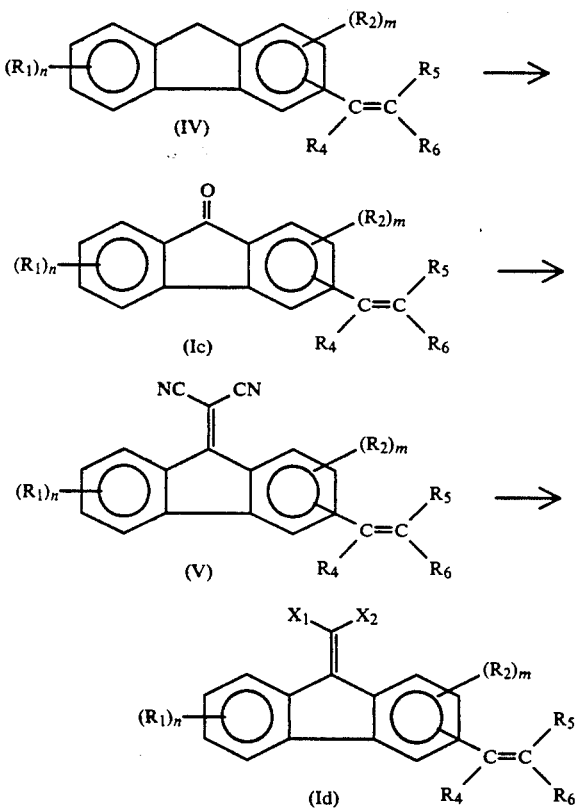

In the above cited formulas, $X_1$, $X_2$, $R_1$, $R_2$, $R_4$, $R_5$, $R_6$, m and n are as defined in formula (I).

The following synthesis examples illustrate the preparation of a number of compounds of formulas (Ic) and (Id).

SYNTHESIS EXAMPLE 4

Synthesis of compounds Ic-(17) and Id-(17)

2-Formylfluorene was reacted with diethyl phenyl phosphonate in the presence of n-butyllithium under reflux in tetrahydrofuran to obtain 2-(2',2'-diphenylvinyl)fluorene (melting point: 136.5°-138° C.). 6.5 g of the 2-(2',2'-diphenylvinyl)fluorene and 100 ml of pyridine were placed in a 150 ml three-necked flask and cooled with ice. 0.5 ml of a 40% aqueous methanol solution of benzyltrimethylammonium hydroxide was added thereto. The mixture was stirred in an oxygen stream for one hour. After completion of the reaction, 100 ml of water was added to the reaction mixture. The resulting yellow precipitate was recovered by filtration and washed with dilute hydrochloric acid and then water. The precipitate was dissolved in methylene chloride, dried over $Na_2SO_4$ and purified by means of silica gel short column (elution with methylene chloride/hexane in a 1/1 ratio). The solvent was distilled off under reduced pressure. The residue was recrystallized from a mixture of ethyl acetate and ethanol to obtain 6.5 g of compound Ic-(17) as an orange yellow needle crystal (melting point: 172°-173.5° C.).

5.0 g of the thus-obtained fluorenone derivative Ic-(17) and 90 ml of pyridine were placed in a 250 ml three-necked flask and heated to 100° C. in a nitrogen stream to dissolve compound Ic-(17). A solution of 1.8 g of malonitrile in 10 ml of pyridine was added dropwise thereto over a period of about 10 minutes. After completion of the addition, the mixture was refluxed for one hour. The reaction mixture was cooled to room temperature and then 100 ml of water was added thereto. The resulting precipitate was recovered by filtration and washed with pyridine, dilute hydrochloric acid, water and then methanol to obtain compound Id-(17) (melting point: 293°-295.5° C.).

SYNTHESIS EXAMPLE 5

Synthesis of compounds Ic-(12) and Id-(12)

2,7-Di-t-butyl-4-chloromethylfluorene was reacted with triphenyl phosphine. The reaction product was condensed with 4-nitrobenzaldehyde to obtain a fluorene compound having the following structural formula.

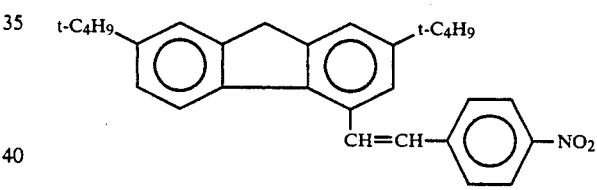

500 mg of the fluorene compound (melting point: 205.5°-207.5° C.), 30 mg of potassium hydroxide and 50 mg of pyridine were placed in a 100 ml round flask and stirred for 20 hours in an air atmosphere at room temperature. After completion of the reaction, 100 ml of water was added thereto. Extraction with methylene chloride was carried out. The organic layer was dried over $Na_2SO_4$. The solvent was distilled off under reduced pressure. The residue was purified by means of silica gel short column (elution with methylene chloride/hexane in a 2/1 ratio). The solvent was distilled off under reduced pressure. The residue was recrystallized from a mixed solution of ethyl acetate and ethanol to obtain 170 mg (yield: 33% by weight) of compound Ic-(12) as a yellow powder (melting point: 223°-224° C.).

110 mg of the fluorenone derivative Ic-(12), 33 mg of malonitrile and 5 ml of pyridine were placed in a 25 ml branched flask. The mixture was refluxed in a nitrogen stream for one hour and pyridine was then distilled. The residue was dissolved in methylene chloride and purified by means of silica gel short column (elution with methylene chloride). The solvent was distilled off under reduced pressure and the residue was washed with methanol and recrystallized from ethyl acetate to obtain 84 mg (yield: 69% by weight) of compound Id-(12) as a reddish brown needle crystal (melting point: 289°–290° C.).

SYNTHESIS EXAMPLE 6

Synthesis of compounds Ic-(6) and Id-(6)

4-Chloromethylfluorene was reacted with triphenyl phosphine. The reaction product was reacted with butyl 4-formylbenzoate to prepare a fluorene compound having the following structural formula.

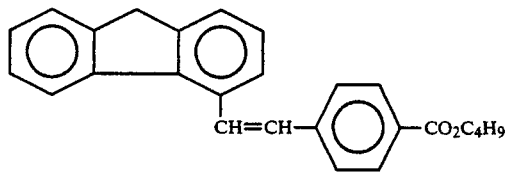

The procedure of Synthesis Example 5 was repeated except that the above fluorene compound was used in place of the fluorene compound of Synthesis Example 5. The product was purified by means of silica gel column to obtain compound Ic-(6)(cis-isomer having a melting point of 96.5°–97.5° C., trans-isomer having a melting point of 116°–117.5° C.).

Further, the compound Id-(6) as a reddish orange needle crystal (melting point: 171°–172° C.) was prepared from the compound Ic-(6) trans-isomer in the same manner as in Synthesis Example 5.

SYNTHESIS EXAMPLE 7

Synthesis of compounds Ic-(8) and Id-(8)

4-Chloromethylfluorene was reacted with triphenyl phosphine. The reaction product was reacted with octyl 4-formylbenzoate to prepare a fluorene compound having the following structural formula.

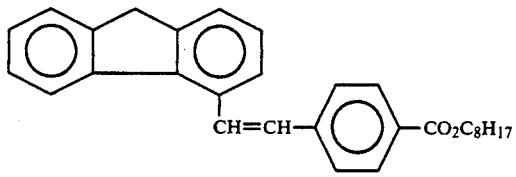

The procedure of Synthesis Example 5 was repeated except that the above fluorene compound was used in place of the fluorene compound of Synthesis Example 5. The product was purified by means of silica gel column to obtain compound Ic-(8) (cis-isomer having a melting point of 81°–83° C., trans-isomer having a melting point of 113.5°–114.5° C.).

Further, the compound Id-(8) as an orange cotton-like crystal (melting point: 142°–144° C.) was prepared from the compound Ic-(8) trans-isomer in the same manner as in Synthesis Example 5.

Although only a few of the compounds encompassed by formulas (Ic) and (Id) were illustratively prepared, methods similar to the methods described above can be used to synthesize the other compounds of formulas (Ic) and (Id).

Examples of electrically conductive substrates which can be used in the present invention include metallic pipes, metallic plates, metallic sheets, metallic foils, high-molecular material films having electrical conductivity imparted thereto, high-molecular material films having a metallized layer such as a layer metallized with a metal such as Al, and high-molecular material films or paper coated with a metal oxide such as $SnO_2$ or a quaternary ammonium salt.

In the electrophotographic photoreceptors of the present invention, a photosensitive layer (light-sensitive layer) is provided on the conductive substrate and the photosensitive layer contains one or more compounds of formula (I) generally in an amount of 10 to 70% by weight, preferably 30 to 60% by weight, based on the weight of the photosensitive layer.

The photosensitive layer may be a single layer structure type or a laminated layer type wherein the charge generating layer and the charge transporting layer are functionally separated from each other.

When the photosensitive layer is of a single layer structure type, the compound of formula (I) as a sensitizing agent may be incorporated in the photosensitive layer comprising conventional materials such as polyvinyl carbazole, or the compound of formula (I) as a charge transporting agent may be incorporated in a binder resin layer containing a conventional charge generating agent. The single layer-type photosensitive layer may contain one or more compounds of formula (I) in an amount of 10 to 70% by weight and preferably 20 to 60% by weight, and the thickness thereof is generally within the range of about 5 to about 30 μm.

When the photosensitive layer is of a laminated layer structure type, the charge generating layer may be formed by depositing a charge generating agent on the conductive substrate or by coating the conductive substrate with a coating solution composed mainly of a charge generating agent and a binder resin.

Any single or mixtures of conventional charge generating agents and any single or mixtures of binder resins can be used. Examples of conventional charge generating agents include inorganic semiconductors such as trigonal selenium, organic semiconductors such as polyvinyl carbazole and organic pigments such as bis-azo compounds, tris-azo compounds, phthalocyanine compounds, pyrylium compounds and squarylium compounds. Examples of the binder resins include polystyrene, silicone resins, polycarbonate resins, acrylic resins, methacrylic resins, polyesters, vinyl polymers, celluloses and alkyd resins.

The thickness of the charge generating layer is generally within the range of about 0.05 to about 10 μm.

The charge transporting layer is formed on the charge generating layer. The charge transporting layer comprises one or more of the compounds of formula (I) and one or more of binder resins. The amount of the compound of formula (I) in the charge transporting layer is generally from 10 to 70% by weight and preferably from 20 to 60% by weight. This charge transporting layer can be formed by coating a coating solution composed mainly of the compound of formula (I), the binder resin, and an appropriate solvent on the charge generating layer by means of an applicator, a bar coater, a dip coater or the like. The weight ratio of the compound of formula (I) and the binder resin is preferably in the range of from about 1/20 to about 20/1.

Any conventional binder resins can be used for the charge transporting layer. Examples of binder resins include styrene-butadiene copolymer, vinyl-toluene-styrene copolymer, styrene-modified alkyd resin, silicone-modified alkyd resin, soybean oil-modified alkyd resin, vinylidene chloride-vinyl chloride copolymer, polyvinyl butyral, nitrated polystyrene, polymethylstyrene, polyisoprene, polyester, phenolic resin, ketone resin, polyamide, polycarbonate, polythiocarbonate, polyvinyl haloarylate, vinyl acetate resin, polystyrene, polyvinyl acrylate, polysulfone and polymethacrylate. If desired, electron-donating materials (positive hole transporting agents) such as tetraphenylbenzidine, triarylamines, hydrazone and stilbene may be added to the charge transporting layer.

The thickness of the charge transporting layer is generally within the range of about 2 to about 100 μm.

In the electrophotographic photoreceptor of the present invention, a barrier layer may be optionally provided on the conductive substrate. The barrier layer is effective in preventing undesired charge injection into the photosensitive layer from the substrate and thus is capable of improving the image quality. Suitable materials for the barrier layer include metal oxides such as aluminum oxide, acrylic resins, phenolic resins, polyester resins and polyurethane.

The present invention is now illustrated in greater detail by reference to the following examples which, however, are not to be construed as limiting the invention in any way.

EXAMPLE 1

A charge generating layer (2.5 μm) composed of trigonal selenium/polyvinyl carbazole (trigonal system selenium: 7% by volume) was provided on an electrically conductive substrate. A solution of 0.5 g of compound Ia-(3) and 0.75 g of bisphenol A polycarbonate (Makrolon 5705, produced by Bayer A.G.) dissolved in 7 g of methylene chloride was coated on the charge generating layer with a gap of 5 mil during wetting and dried at 80° C. for one hour to prepare an electrophotographic photoreceptor. The electrophotographic photoreceptor was charged with electricity at +800 V and −800 V by using an electrostatic copying paper testing equipment (SP428, manufactured by Kawaguchi Denki Seisakusho K.K.) and exposed to white light of 5 lx. Sensitivity (dv/dt) was measured. The above discussed procedure was repeated to prepare various electrophotographic photoreceptors except that in place of compound Ia-(3), each of the following compounds was used: Ib-(3), Ic-(6) and Id-(6). The results are shown in Table 1.

TABLE 1

| Compound | Initial Sensitivity (V/sec) +800 V | −800 V |
|---|---|---|
| Ia-(3) | 530 | —* |
| Ib-(3) | 2015 | — |
| Ic-(6) | 153 | — |
| Id-(6) | 190 | — |

* "—" means that no light decay was observed.

EXAMPLE 2

The procedure of Example 1, regarding the production of a photoreceptor containing compound Ia-(3), was repeated except that each of compounds Ia-(5), (7), (10), (11), (12) and (15) was used in place of compound Ia-(3) to prepare electrophotographic photoreceptors. Sensitivity was measured in the same manner as that described above. The results are shown in Table 2.

EXAMPLE 3

The procedure of Example 1, regarding the production of a photoreceptor containing compound Ib-(3), was repeated except that each of compounds Ib-(5), (7), (10), (11), (12), (15), (18) and (20) was used in place of compound Ib-(3) to prepare electrophotographic photoreceptors. Sensitivity was measured in the same manner as that described above. The results are shown in Table 2.

EXAMPLE 4

The procedure of Example 1, regarding the production of a photoreceptor containing compound Ic-(6), was repeated except that each of compounds Ic-(3), (8), (9), (10), (12), (13), (16) and (17) was used in place of compound Ic-(6) to prepare electrophotographic photoreceptors. Sensitivity was measured in the same manner as that described above. The results are shown in Table 2.

EXAMPLE 5

The procedure of Example 1, regarding the production of a photoreceptor containing compound Id-(6), was repeated except that each of compounds Id-(3), (8), (9), (10), (12), (13), (16), (17), (21), (23) and (24) was used in place of compound Id-(6) to prepare electrophotographic photoreceptors. Sensitivity was measured in the same manner as that described above. The results are shown in Table 2.

COMPARATIVE EXAMPLE 1

The procedure of Example 1 was repeated except that 2,4,7-trinitrofluorenone (TNF) was used in place of the compound of formula (I) to prepare an electrophotographic photoreceptor. Sensitivity was measured in the same manner as that described above. The results are shown in Table 2.

TABLE 2

| | Added Compound | Initial Sensitivity +800 V | −800 V |
|---|---|---|---|
| Example 2 | Ia-(5) | 325 | —* |
| | Ia-(7) | 481 | — |
| | Ia-(10) | 350 | — |
| | Ia-(11) | 295 | — |
| | Ia-(12) | 353 | — |
| | Ia-(15) | 206 | — |
| Example 3 | Ib-(5) | 1215 | — |
| | Ib-(7) | 1930 | — |
| | Ib-(10) | 1535 | — |
| | Ib-(11) | 1120 | — |
| | Ib-(12) | 1450 | — |
| | Ib-(15) | 730 | — |
| | Ib-(18) | 215 | — |
| | Ib-(20) | 435 | — |
| Example 4 | Ic-(3) | 75 | — |
| | Ic-(8) | 163 | — |
| | Ic-(9) | 164 | — |
| | Ic-(10) | 121 | — |
| | Ic-(12) | 74 | — |
| | Ic-(13) | 75 | — |
| | Ic-(16) | 83 | — |
| | Ic-(17) | 75 | — |
| Example 5 | Id-(3) | 83 | — |
| | Id-(8) | 205 | — |
| | Id-(9) | 195 | — |
| | Id-(10) | 152 | — |
| | Id-(12) | 70 | — |
| | Id-(13) | 97 | — |
| | Id-(16) | 71 | — |
| | Id-(17) | 68 | — |
| | Id-(21) | 175 | — |
| | Id-(23) | 89 | — |
| | Id-(24) | 132 | — |
| Comp. Ex. 1 | TNF | 66 | — |

*See Table 1

EXAMPLE 6

A solution of 0.5 of compound Ia-(3) and 0.75 g of polyvinyl carbazole dissolved in 7 g of methylene chloride was coated on an electrically conductive substrate with a gap of 5 mil during wetting and dried at 80° C. for one hour to prepare an electrophotographic photoreceptor. The electrophotographic photoreceptor was charged with electricity at +800 V and −800 V by using an electrostatic copying paper testing equipment (SP428, manufactured by Kawaguchi Denki Seisakusho K.K.) and exposed to white light of 5 lx. Sensitivity (dv/dt) was measured. The above discussed procedure was repeated to prepare various electrophotographic photoreceptors except that in place of compound Ia-(3), each of the following compounds was used: Ib-(3), Ic-(6), and Id-(6). The results are shown in Table 3.

TABLE 3

| Exemplified Compound | Initial Sensitivity (V/sec) | |
|---|---|---|
| | +800 V | −800 V |
| Ia-(3) | 465 | 177 |
| Ib-(3) | 1973 | 182 |
| Ic-(6) | 235 | 174 |
| Id-(6) | 375 | 180 |

EXAMPLE 7

The procedure of Example 6, regarding the production of a photoreceptor containing compound Ia-(3), was repeated except that each of compounds Ia-(5), (7), (10), (11), (12) and (15) was used in place of compound Ia-(3) to prepare electrophotographic photoreceptors. Sensitivity was measured in the same manner as that described above. The results are shown in Table 4.

EXAMPLE 8

The procedure of Example 6, regarding the production of a photoreceptor containing compound Ib-(3), was repeated except that each of compounds Ib-(5), Ib-(7), Ib-(10), (11), Ib-(12), (15), (18) and (20) was used in place of compound Ib-(3) to prepare electrophotographic photoreceptors. Sensitivity was measured in the same manner as that described above. The results are shown in Table 4.

EXAMPLE 9

The procedure of Example 6, regarding the production of a photoreceptor containing compound Ic-(6), was repeated except that each of compounds Ic-(3), (8), (9), (10), (12), (13), (16), (17) and (20) was used in place of compound Ic-(6) to prepare electrophotographic photoreceptors. Sensitivity was measured in the same manner as that described above. The results are shown in Table 4.

EXAMPLE 10

The procedure of Example 6, regarding the production of a photoreceptor containing compound Id-(6), was repeated except that each of compounds Id-(3), (8), (9), (10), (12), (13), (16), (17), (21), (23) and (24) was used in place of compound Id-(6) to prepare electrophotographic photoreceptors. Sensitivity was measured in the same manner as that described above. The results are shown in Table 4.

COMPARATIVE EXAMPLE 2

The procedure of Example 6 was repeated except that 2,4,7-trinitrofluorenone (TNF) was used in place of the compound of formula (I) to prepare an electrophotographic photoreceptor. Sensitivity was measured in the same manner as that described above. The results are shown in Table 4.

TABLE 4

| | Added Compound | Initial Sensitivity | |
|---|---|---|---|
| | | +800 V | −800 V |
| Example 7 | Ia-(5) | 354 | 175 |
| | Ia-(7) | 426 | 161 |
| | Ia-(10) | 452 | 185 |
| | Ia-(11) | 313 | 179 |
| | Ia-(12) | 308 | 155 |
| | Ia-(15) | 254 | 163 |
| Example 8 | Ib-(5) | 1305 | 193 |
| | Ib-(7) | 1590 | 171 |
| | Ib-(10) | 1715 | 166 |
| | Ib-(11) | 1230 | 184 |
| | Ib-(12) | 1255 | 182 |
| | Ib-(15) | 945 | 165 |
| | Ib-(18) | 305 | 173 |
| | Ib-(20) | 510 | 175 |
| Example 9 | Ic-(3) | 104 | 192 |
| | Ic-(8) | 473 | 195 |
| | Ic-(9) | 205 | 189 |
| | Ic-(10) | 214 | 213 |
| | Ic-(12) | 159 | 195 |
| | Ic-(13) | 204 | 190 |
| | Ic-(16) | 103 | 233 |
| | Ic-(17) | 186 | 201 |
| | Ic-(20) | 165 | 172 |
| Example 10 | Id-(3) | 132 | 183 |
| | Id-(8) | 510 | 170 |
| | Id-(9) | 254 | 185 |
| | Id-(10) | 320 | 193 |
| | Id-(12) | 205 | 182 |
| | Id-(13) | 224 | 161 |
| | Id-(16) | 155 | 191 |
| | Id-(17) | 230 | 173 |
| | Id-(21) | 507 | 181 |
| | Id-(23) | 213 | 182 |
| | Id-(24) | 305 | 175 |
| Comp. Ex. 2 | TNF | 154 | 165 |

It is apparent from the comparison between the examples and the comparative examples that the compounds of formula (I) exhibit superior charge transporting ability as compared with TNF which is already known as having a good charge transporting ability. Therefore, the electrophotographic photoreceptors obtained by inclusion of compounds of formula (I) have excellent electrophotographic characteristics. Particularly, when the compounds of formula (I) are used as charge transporting agents in the charge transporting layer of the laminated layer type electrophotographic photoreceptors, there is obtained positively charging type electrophotographic photoreceptors having excellent electrophotographic characteristics.

While the present invention has been described in detail and with reference to specific embodiments thereof, it is apparent to one skilled in the art that various changes and modifications can be made therein without departing from the spirit and the scope of the present invention.

What is claimed is:

1. An electrophotographic photoreceptor comprising a conductive substrate and a photosensitive layer on the conductive substrate, wherein the photosensitive layer comprises a charge generating agent and a compound of formula (I):

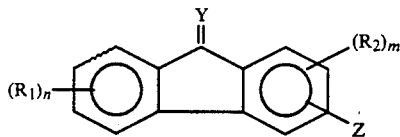

wherein $R_1$ and $R_2$ each represents a hydrogen atom, an alkyl group, an aryl group, an alkoxycarbonyl group, an aryloxycarbonyl group, a nitro group, a halogen atom, an alkylcarbonyl group or an arylcarbonyl group; Y represents

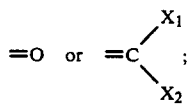

$X_1$ and $X_2$ may be the same or different groups and are selected from a cyano group or an alkoxycarbonyl group; Z represents

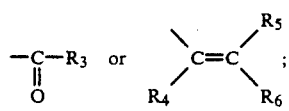

$R_3$ represents a substituted or unsubstituted aryl or nitrogen-containing heterocyclic group; $R_4$, $R_5$ and $R_6$ each represents a hydrogen atom, an alkyl group, an aralkyl group, an aryl group or a heterocyclic group; when Z is the

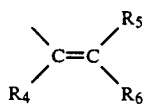

group, $R_1$ and $R_2$ are other than the alkylcarbonyl group; m is 0 or 1; n is 0 to 2; and when n is 2, the $R_1$ groups may be the same or different.

2. The electrophotographic photoreceptor according to claim 1, wherein the photosensitive layer comprises a compound of formula (Ia):

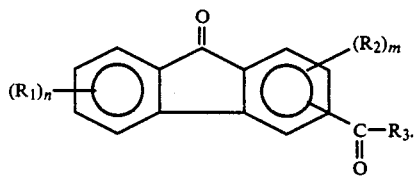

3. The electrophotographic photoreceptor according to claim 1, wherein the photosensitive layer comprises a compound of formula (Ib):

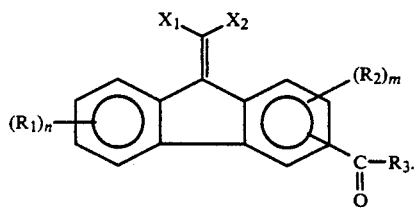

4. The electrophotographic photoreceptor according to claim 1, wherein the photosensitive layer comprises a compound of formula (Ic):

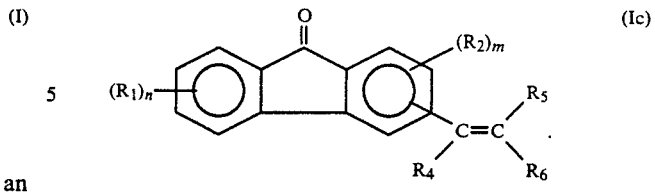

5. The electrophotographic photoreceptor according to claim 1, wherein the photosensitive layer comprises a compound of formula (Id):

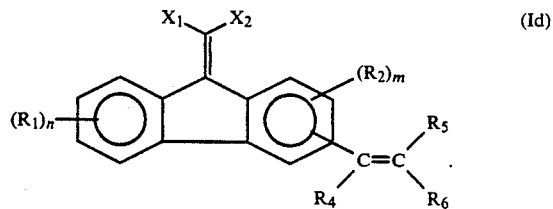

6. The electrophotographic photoreceptor according to claim 1, wherein the photosensitive layer contains from 10 to 70% by weight of the compound of formula (I).

7. The electrophotographic photoreceptor according to claim 1, wherein the charge generating agent is selected from the group consisting of inorganic semiconductor materials, organic semiconductor materials, bis-azo compounds, tris-azo compounds, phthalocyanine compounds, pyrylium compounds, and squarylium compounds.

8. The electrophotographic photoreceptor according to claim 1, wherein the photosensitive layer comprises a charge generating layer and a charge transporting layer.

9. The electrophotographic photoreceptor according to claim 8, wherein the charge transporting layer comprises the compound of formula (I) and a binder resin.

10. The electrophotographic photoreceptor according to claim 9, wherein the binder resin is selected from the group consisting of styrene/butadiene copolymer, vinyltoluene/styrene copolymer, styrene-modified alkyd resin, silicone-modified alkyd resin, soybean oil-modified alkyd resin, vinylidene chloride/vinyl chloride copolymer, polyvinyl butyral, nitrated polystyrene, polymethylstyrene, polyisoprene, polyester, phenolic resin, ketone resin, polyamide, polycarbonate, polythiocarbonate, polyvinyl haloarylate, vinyl acetate resin, polystyrene, polyvinylacrylate, polysulfone, and polymethacrylate.

11. The electrophotographic photoreceptor according to claim 9, wherein the charge transporting layer contains from 10 to 70% by weight of the compound of formula (I).

12. The electrophotographic photoreceptor according to claim 8, wherein the charge generating layer is from about 0.05 to about 10 μm thick and the charge transporting layer is from about 2 to about 100 μm thick.

13. The electrophotographic photoreceptor according to claim 9, wherein the charge transporting layer additionally comprises an electron donating material.

14. The electrophotographic photoreceptor according to claim 1, further comprising a barrier layer between the conductive substrate and the photosensitive layer.

15. A photosensitive layer useful in an electrophotographic photoreceptor comprising a charge generating agent and the compound of formula (I) as set forth in claim 1.

* * * * *